United States Patent [19]

Kurtz et al.

[11] E Re. 29,877

[45] Reissued Jan. 9, 1979

[54] VALVED UNDERWATER DRAINAGE APPARATUS

[75] Inventors: Leonard D. Kurtz, Woodmere; Robert E. Bidwell, Melville, both of N.Y.

[73] Assignee: Deknatel Inc., Queens Village, N.Y.

[21] Appl. No.: 808,982

[22] Filed: Jun. 22, 1977

Related U.S. Patent Documents

Reissue of:

[64] Patent No.: 3,853,128
Issued: Dec. 10, 1974
Appl. No.: 269,962
Filed: Jul. 10, 1972

[51] Int. Cl.[2] ..... A61F 5/44
[52] U.S. Cl. ..... 128/275
[58] Field of Search ..... 128/275–278, 128/294–295

[56] References Cited

U.S. PATENT DOCUMENTS

| | | | |
|---|---|---|---|
| 3,363,626 | 1/1968 | Bidwell et al. | 128/276 |
| 3,376,868 | 4/1968 | Mondiadis | 128/278 |
| 3,381,687 | 5/1968 | Andersen et al. | 128/276 |
| 3,599,639 | 8/1971 | Spotz | 128/276 |
| 3,738,870 | 6/1973 | Schachet | 128/277 |
| 3,757,783 | 9/1973 | Alley | 128/276 |

FOREIGN PATENT DOCUMENTS

| | | | |
|---|---|---|---|
| 1148709 | 5/1963 | Fed. Rep. of Germany | 128/276 |

*Primary Examiner*—Dalton L. Truluck
*Attorney, Agent, or Firm*—Larson, Taylor and Hinds

[57] ABSTRACT

A drainage apparatus for evacuating fluids from cavities including a collection chamber for collecting fluids from the body cavity, a water seal chamber and a pressure regulator chamber. A valve mechanism is provided in the water seal chamber to permit the outflow of gases from the apparatus in the event of a sudden increase in pressure in the device due to respiratory movements or leakage of air.

4 Claims, 4 Drawing Figures

VALVED UNDERWATER DRAINAGE APPARATUS

Matter enclosed in heavy brackets [ ] appears in the original patent but forms no part of this reissue specification; matter printed in italics indicates the additions made by reissue.

This invention relates to a drainage apparatus and more particularly to an apparatus for draining fluids from a body cavity, commonly referred to as an underwater drainage apparatus.

In U.S. Pat. No. 3,363,626 issued Jan. 16, 1968 there is disclosed an underwater drainage apparatus of a one piece, unitary construction. This device includes a collection or trap chamber for collecting liquids from a body cavity, a water seal chamber which prevents the passage of air from atomsphere into the body cavity, a manometer chamber which regulates the degree of vacuum imposed in the system. Under normal operating conditions the collection chamber is connected by a thoracotomy tube to a patient's pleural cavity. The device is connected to a suction pump and the amount of liquid inthe manometer chamber determines the degree of vacuum imposed. This system functions exceedingly well under most conditions. However, certain respiratory ailments and conditions result in sudden increases of pressure in the pleural cavity. For example, a cough will produce a rapid increase in the pressure in the pleural cavity and it is desirable to provide means which will permit the sudden high pressure to be exhausted from the system immediately without imposing a back pressure on the patient.

In the system disclosed in U.S. Pat. No. 3,363,626 a sudden increase in pressure in the patient's pleural cavity sometimes causes the water in the manometer chamber to be forced out into atmosphere. This renders the manometer chamber inoperative and reduces the negativity imposed on the patient's pleural cavity.

According to the present invention there is provided a valve in the water seal chamber which connects the water seal chamber with atmosphere. During normal operating conditions when a substantial degree of negativity is maintained in the water seal chamber, this valve will remain closed. However, in the event of a sudden increase in pressure within the pleural cavity the valve will open thereby permitting the gas to escape to atmosphere and reduce the pressure within the underwater drainage apparatus and pleural cavity. As soon as the pressures are reduced the valve will close and normal operating conditions will be resumed.

An object of the present invention is to provide an underwater drainage apparatus with valve means to prevent sudden increases in pressure within the pleural cavity.

Another object of the present invention is to provide a valve in the wall of the seal chamber in an underwater drainage apparatus to prevent sudden increases in pressure within the pleural cavity.

Other objects and many of the attendant advantages of the present invention will become more readily apparent upon consideration of the following detailed specification in connection with the accompanying drawing wherein.

Figure 1:
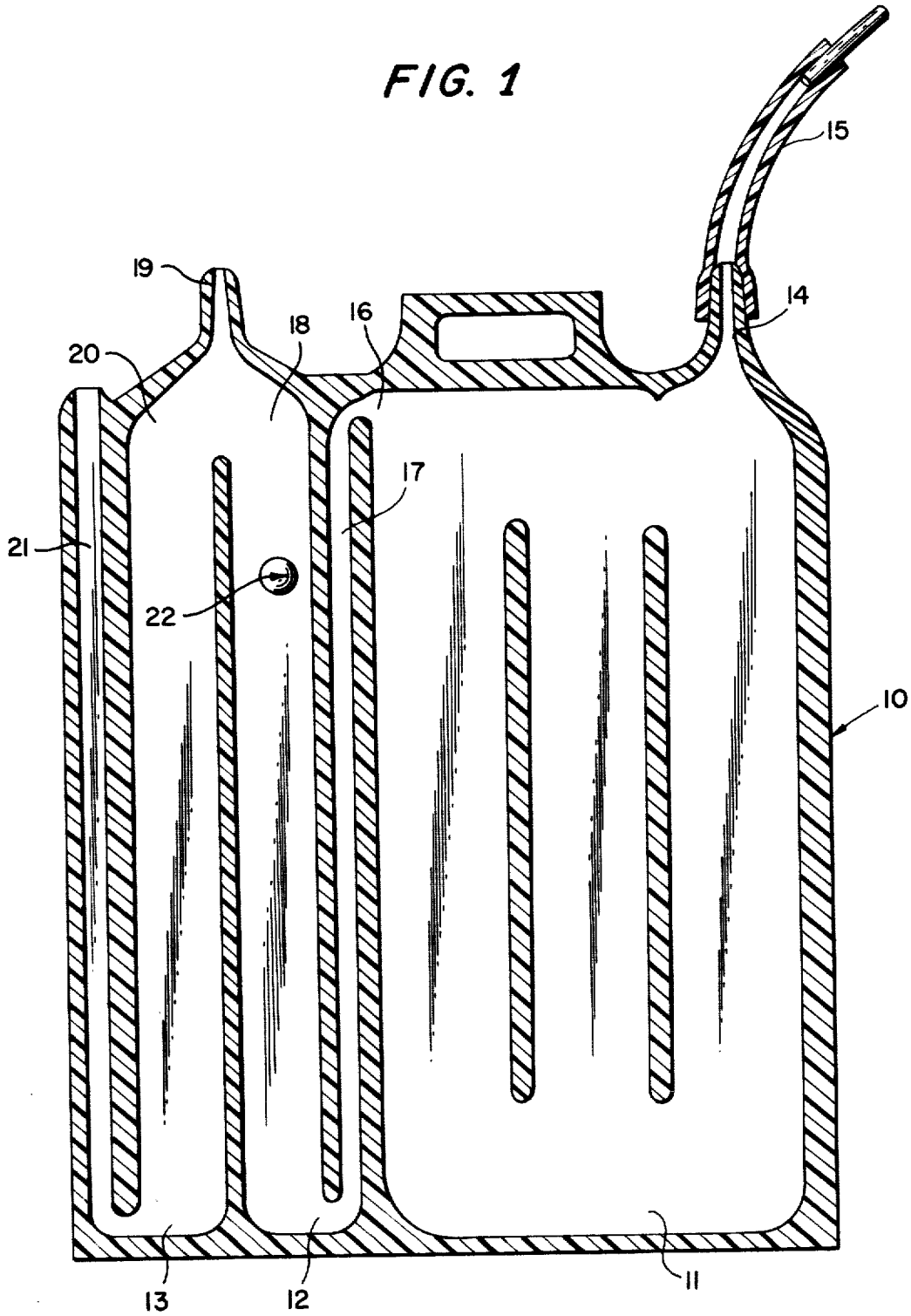
FIG. 1 is a sectional view through an underwater drainage apparatus.

Referring now more particularly to FIG. 1 there is shown an underwater drainage device 10 which may be of a one piece construction and molded of plastic or like material. The device comprises a collection or trap chamber 11, a generally U-shaped water seal chamber 12 and a manometer chamber 13.

The collection chamber 11 is provided with an inlet 14 which is connected by means of a thoracotomy tube 15 with the patient's pleural cavity to be drained. The collection chamber 11 has an outlet 16 in communication with the inlet at the upper end of arm 17 of the U-shaped water seal chamber 12. The upper end of the other arm 18 of the U-tube water seal chamber 12 communicates with a suction outlet 19 and with the upper end of arm 20 of the U-tube forming the manometer chamber 13. The other arm 21 of the manometer chamber is open to atmosphere as shown.

The specific manner in which the underwater drainage apparatus described herein operates is more fully set forth in prior U.S. Pat. No. 3,363,626. In general liquid is placed in the water seal chamber 12 and in the manometer chamber 13 with the outlet 19 connected to a source of suction. When the thoracotomy tube 15 is placed in communication with the patient's pleural cavity, a vacuum is imposed thereon, the degree of vacuum being determined by the amount of water within the manometer chamber 13. Fluids within the pleural cavity are drawn out through the thoracotomy tube with the liquids falling into the collection chamber 11 and gases passing through the water seal chamber 17 and 18 and through the suction outlet.

It has been found that certain respiratory conditions will cause a sudden increase in the pressure within the pleural cavity. For example, a cough or an air leak will produce a sudden substantially higher pressure within the pleural cavity which must be expelled in order to permit normal respiratory action. In the underwater drainage apparatus as described in U.S. Pat. No. 3,363,626 such a sudden increase in pressure will cause the gases to pass through the collection chamber, through the water seal chamber and may force water out of the manometer chamber as the gases pass out through the opening to atmosphere. Such an occurrence would cause a substantial amount of the liquid in the manometer chamber to be lost and, upon return to lower pressures in the pleural cavity, a substantially lower vacuum will be imposed on the cavity by reason of the loss of water in the manometer chamber. In fact, under certain extreme conditions, all of the water in the manometer chamber may be lost and consequently the suction pump would be ineffective to produce any increased vacuum in the pleural cavity.

According to the present invention there is provided a valve within the wall of the water seal chamber, such valve being identified generally in FIG. 1 at 22. It is to be noted that this valve is disposed within the large arm 18 of the water seal chamber 12 and the valve will normally remain in a closed position and will open only in response to a substantially increased pressure within the water seal chamber 12.

Figure 4:
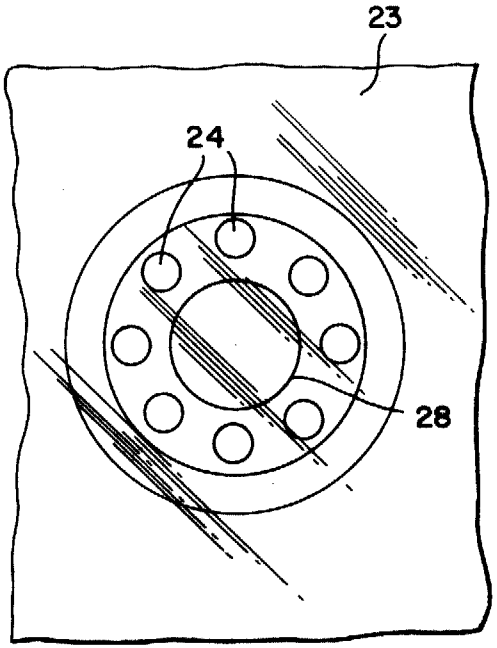
FIG. 4 is a face view of the exterior wall of the water seal chamber showing the valve openings.
Figure 3:
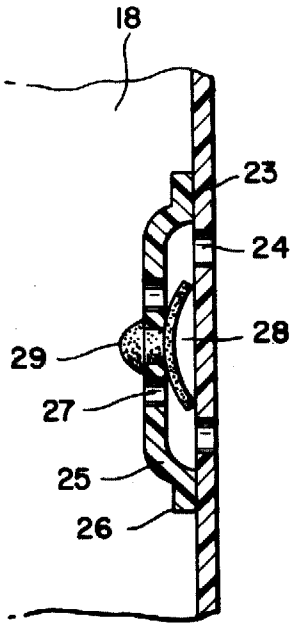
FIG. 3 is a view similar to FIG. 2 showing the valve in open position.
Figure 2:
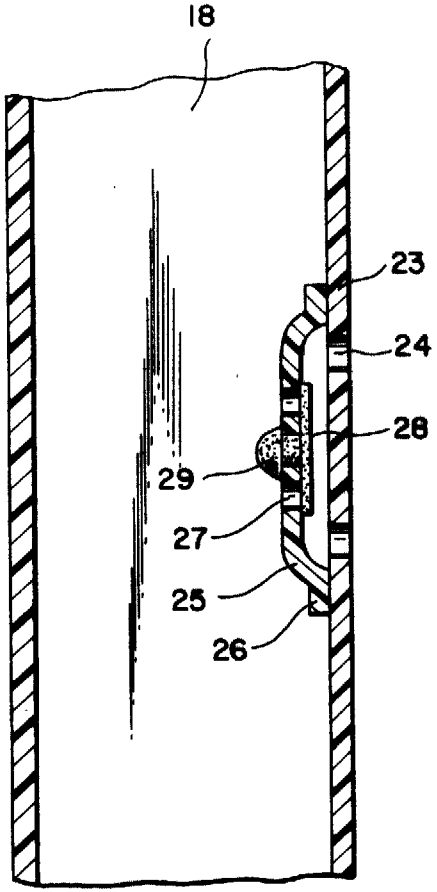
FIG. 2 is a sectional view through the valve.

Referring more particularly to FIGS. 2 to 4 inclusive the wall of the water seal chamber 18 is shown at 23. As can be seen in FIG. 4 the exterior wall is provided with a series of apertures 24 arranged in a circular pattern. Secured to the inner face of wall 23 is a plate 25 in the form of a disc having a circular peripheral flange 26 and a recessed central portion. The recessed central portion of plate 25 is provided with apertures 27 which are disposed in a circular arrangement similar to the apertures 24 on exterior wall 23. Secured to plate 25 at the center thereof is a resilient disk valve 28, this disk valve having a central extension or protuberance 29 which passes through an aperture in the plate 25 to secure the disk to the plate. The disk 28 covers the apertures 27 in plate 25 as shown in FIG. 2.

During normal operation of the underwater drainage apparatus the reduced pressure within the device will maintain the valve 28 closed inasmuch as atmospheric pressure will be acting against the outer face of the valve. However, during a cough or air leakage condition within the pleural cavity creating a momentary high pressure condition within the apparatus the valve will open as shown in FIG. 3 so as to permit the excess gas to pass outwardly through the apertures 27 and 24. When normal pressure conditions within the apparatus are regained the valve will return to the closed position.

While the valve is shown as used with an underwater drainage device as disclosed in U.S. Pat. No. 3,363,626, it is obvious that this valve mechanism may be used in conjunction with the modifications of the apparatus shown in the aforementioned patent, such modifications and improvements being shown for example in U.S. Pat. No. 3,363,627 and U.S. Pat. No. 3,559,647.

It is also readily apparent that the valve mechanism could function equally well when mounted at other locations within the underwater drainage apparatus. For example, the valve 22 could be disposed within a wall of the collection chamber, most conveniently towards the upper end of this chamber. Alternatively the valve could be located in the other arm 17 of the water seal chamber, in the manometer chamber large arm 20 or even in the thoracotomy tube itself. The function of the valve 22, as described hereinbefore, is to permit the escape of gas within the drainage device when a sudden increase in pressure occurs within the device and this function can be performed with the valve located at various points within the device.

The valve mechanism is shown as used on a three bottle system but could be used in a two or one bottle underwater drainage system. In a two bottle system the valve could be located in the underwater seal chamber, in the collection chamber or in the thoracotomy tube.

In a one bottle system the valve may be located in the collection chamber or in the thoracotomy tube.

We claim:

1. In an underwater drainage device for draining fluid from a pleural cavity comprising a collection chamber having an inlet, a thoracotomy tube interconnecting the pleural cavity and the inlet to said collection chamber whereby the collection chamber receives and collects fluids drained from the pleural cavity, an outlet from the collection chamber, a U-shaped water seal chamber, a U-shaped manometer chamber, the upper end of one arm of the U-shaped water seal chamber being connected to the outlet from the collection chamber, the upper end of the other arm of the U-shaped water seal chamber being connected to the upper end of one arm of the U-shaped manometer chamber, the other arm of the U-shaped manometer chamber being open to atmosphere, a connection from said device with a source of suction, during normal operation the source of suction maintaining the pleural cavity at a negative pressure determined by the fluid in the manometer chamber, and *check* valve means *disposed* in said device *between the water seal of the water seal chamber and the lower part of the U-shaped manometer chamber on the normally lower pressure side thereof,* said *check* valve means being normally closed and opening only during sudden abnormal conditions when the pressure within the pleural cavity exceeds atmospheric pressure, said valve means being an outlet to atmosphere in addition to the outlet to atmosphere provided by the arm of the U-shaped manometer chamber open to atmosphere, said valve means being positioned in said device to vent to atmosphere sudden positive pressure surges within the pleural cavity occurring even during normal operation of the suction source and to prevent said sudden positive pressure surges from causing fluid within the U-shaped manometer chamber from passing out through the arm open to atmosphere to vary the degree of vacuum imposed by the source of suction.

2. In an underwater drainage device according to claim 1 wherein said *check* valve means is disposed in said device on the low pressure side of the U-shaped manometer chamber.

3. In an underwater drainage device according to claim 1 wherein said *check* valve comprises an opening to atmosphere in a wall of said device and means covering said [openings] *opening* to atmosphere when the pressure within said device is less than atmosphere.

*4. In an underwater drainage device according to claim 1 wherein said check valve means comprising a mechanical seating member and a mechanical valve member engagable with said seating member such that when said valve member engages said seating member, said valve is closed and when said valve member does not engage said seating member said valve is open.*

* * * * *